United States Patent [19]

Renard et al.

[11] Patent Number: 4,813,967
[45] Date of Patent: Mar. 21, 1989

[54] PROCESS FOR FORMING A PIECE SURGICALLY IMPLANTABLE IN AN ORGANISM AND A PIECE THUS OBTAINED

[75] Inventors: Pierre Renard, Etampes; Jean-Louis Chareire, Courbevoie, both of France

[73] Assignee: Societe Nationale Industrielle Aerospatiale, Paris, France

[21] Appl. No.: 97,337

[22] Filed: Sep. 11, 1987

Related U.S. Application Data

[63] Continuation of Ser. No. 833,410, Jan. 17, 1986, abandoned.

[30] Foreign Application Priority Data

Jun. 19, 1984 [FR] France .............................. 84 09573

[51] Int. Cl.[4] .......................... A61F 2/10; C04B 40/00
[52] U.S. Cl. .................................... 623/66; 623/11; 427/2; 264/82
[58] Field of Search ................... 623/16, 66, 13, 11; 128/335.7; 427/2; 264/81, 82

[56] References Cited

U.S. PATENT DOCUMENTS

| | | | |
|---|---|---|---|
| 3,442,617 | 5/1969 | Turkat et al. | 264/81 |
| 3,663,965 | 5/1972 | Lee et al. | 3/1 |
| 3,783,868 | 1/1974 | Bokros | 623/66 X |
| 3,867,190 | 2/1975 | Schmitt et al. | 427/2 |
| 3,893,196 | 7/1975 | Hochman | 623/23 X |
| 4,129,470 | 12/1978 | Homsy | 623/66 X |
| 4,183,357 | 1/1980 | Bentley et al. | 623/66 X |
| 4,321,914 | 3/1982 | Begovac et al. | 128/1 |
| 4,344,435 | 8/1982 | Aubin | 128/350 |
| 4,377,010 | 3/1983 | Fydelor et al. | 623/15 X |
| 4,410,577 | 10/1983 | Palmer et al. | 428/259 X |
| 4,512,038 | 4/1985 | Schmitt et al. | 427/2 |

FOREIGN PATENT DOCUMENTS

| | | |
|---|---|---|
| 2105998 | 4/1972 | France . |
| 2135326 | 12/1972 | France . |
| 2350825 | 12/1977 | France . |
| 2427315 | 12/1979 | France . |
| 2427197 | 12/1979 | France . |
| 2056282 | 3/1981 | United Kingdom . |
| 2092891 | 8/1982 | United Kingdom . |
| 8100808 | 4/1981 | World Int. Prop. O. . |

*Primary Examiner*—Richard J. Apley
*Assistant Examiner*—Alan W. Cannon
*Attorney, Agent, or Firm*—Fisher, Christen & Sabol

[57] ABSTRACT

A process for forming a piece (6) implantable in an organism, more especially for the percutaneous passage of cables or pipes (8).

According to the invention, the piece (6) is formed from a felt of carbon fibers coated with a pyrocarbon matrix.

5 Claims, 1 Drawing Sheet

PROCESS FOR FORMING A PIECE SURGICALLY IMPLANTABLE IN AN ORGANISM AND A PIECE THUS OBTAINED

This application is a continuation of application Ser. No. 833,410, filed Jan. 17, 1986, now abandoned.

The present invention concerns a process for forming a piece surgically implantable in an organism and the piece thus obtained.

It is known that if a foreign body is introduced into an organism, a natural defense mechanism thereof causes its cells to isolate said foreign body. For example, if a splinter is lodged in the skin, the cells of the epiderm surround it with a sealed envelope and work round it so as to try to reject it outwardly. In addition, if a foreign body of great length, such as thread or a tube, passes through the skin, this latter over the whole of its thickness covers said body with a non adherent sheath of epithelial cells. In this case, it is obvious that microbes may be permanently introduced between the foreign body and said sheath, so that a center of infection results therefrom.

The present invention has an object to overcome these drawbacks and to allow a surgically implantable biocompatible piece to be formed capable not only of not being rejected by said organism but further of being integrally joined with the tissues in which it is implanted.

To this end, in accordance with the invention, the process for forming a carbon fiber based piece surgically implantable in an organism is remarkable in that a bed is formed of carbon fiber sections whose length is at most equal to 30 mm, said sections resting freely on each other with random orientations;

said bed is subjected to compressions so that its specific mass is between 0.05 and 0.3 $g/cm^2$;

said bed thus compressed is introduced into an enclosure containing a hydrocarbonated gas and said gas is subjected to the conditions of its cracking, so that pyrocarbon is deposited on the fiber sections forming said bed; and cracking of said hydrocarbonated gas is continued until said bed of carbon fiber sections reaches a specific mass between 0.5 and 1.6 $g/cm^3$.

Thus a biocompatible porous composite structure is obtained formed of a carbon frame whose fiber sections are coated with a pyrocarbon matrix. Tests have shown that the cells of the tissues surrounding an implanted piece having such a structure presented such an affinity with said piece that they are firmly fixed thereto before the rejection phenomenon can begin to appear. Consequently, an implantable piece in accordance with the invention, is not only not rejected by the organism but is further firmly fixed to the living tissues which surround it, since the cells of said tissues (fibroblasts) colonise it over the whole of its thickness.

It will be noted that the patents U.S. Pat. No. 3,992,725 and U.S. Pat. No. 4,129,470 described a surgically implantable piece having a carbon fiber basis. However, in this case, the carbon fibers are joined together by polytetrafluoroethylene, so that the pores of the structure are sealed in their large majority. The result is that the anchorage positions of the living tissues on the piece are not as numerous as they could be and the rapidity and the quality of the connection between the piece and the tissues are not optimum.

In the present invention, on the contrary, during cracking of the hydrocarbonated gas, the pyrocarbon is deposited solely on the fiber sections while enlarging the diameter thereof, and such a deposit is formed practically uniformly over the whole length of said sections, since the hydrocarbonated gas passes freely between the carbon sections forming the compressed bed.

Consequently, although the pyrocarbon deposit reduces the dimensions of the pores existing between the fiber sections of the compressed bed, the number of said pores remains the same so that the piece obtained is particularly porous and has communicating pores.

It will be readily understood that by controlling the cracking of the hydrocarbonated gas, the best possible compromise may be obtained between the dimensions of the pores of the piece and the solidity thereof, given by the pyrocarbon matrix.

When it is desired to confer on the piece obtained by the process of the invention mechanical properties reinforced in a direction perpendicular to said bed, for example for providing wear surfaces or holes orientated in this way, it is advantageous to subject said bed of carbon fiber sections, preferably after compression, to tufting in a direction orthogonal to the multiple coplanar directions of said sections. Thus a sort of tufted felt of carbon fibers is obtained which is then possibly compressed and receives the pyrocarbon matrix.

To give its final form to the piece obtained by using the process of the invention, it may be necessary to machine it. In this case, so as to prevent the machining cuttings on the one hand from remaining fixed to the machined piece and from spreading consequently into the organism and on the other hand for preventing fragile surface particles from being detached after implantation, said machined piece is subjected to very active cleaning which comprises not only a thorough removal of dust, but also the application of ultrasounds for eliminating said particles weakly adhering to the rest of said piece.

Such cleaning may also comprise oxidization of the machined piece at a high temperature (for example a 1000° C.), for a few seconds in an oxygen atmosphere. Such oxidization allows not only the combustion and elimination of free particles due to machining as well as the rounding off of the fragile micro roughnesses but also the formation of oxygenated groups, for example of the carboxyl type, which are fixed on the piece. Subsequently, if said piece is heated (for example at 1500° C.) under a vacuum ($10^{-3}$ torrs), the oxygen of these oxygenated groups is released so that free radicals appear allowing the grafting of atoms or molecules (lactide, muco-polysaccharide, halogen, ...) capable of promoting the fixation of living cells. In this case, the fixation of the living cells on the piece is therefore not only physical (engagement of the cells in the pores of the piece), but also chemical.

It is in addition, advantageous, before implantation of the piece in the organism, to impregnate it with a nutritive serum for the cells. Thus the life of the cells is promoted during their initial growth inside the pores of the piece. Such a nutritive serum may be of the type used for the in vitro culture of similar cells.

Thus a piece surgically implantable in an organism is remarkable in that it has a composite structure comprising a framework of carbon fiber sections whose length is at most equal to 30 mm and which form a bed in which said sections are coated with pyrocarbon joining them to each other, the specific mass of this composite structure being between 0.5 and 1.6 g/cm.

Preferably, said framework forms a tufted felt of carbon fiber sections and a diameter of said fibers is of the order of 8 to 12 microns.

Although not exclusively, the implantable piece of the invention is particularly well adapted to the construction of a percutaneous passage device, such for example as described in patent U.S. Pat. No. 3,663,965, U.S. Pat. No. 3,783,868, U.S. Pat. No. 4,321,914, U.S. Pat. No. 4,344,435 and GB-A-2 056 282, comprising a tubular part integral with a collar at one of its ends.

Preferably, according to a feature of the invention, the outer wall of the tubular part has the form of a coaxial cone at said tubular part and is joined to said collar, on the same side as its base. The slant of the generatrices of the cone with respect to said collar is advantageously between 30° and 60°.

So as to further increase the solidness of the connection between the piece and the living tissue, at least one annular groove with rounded edges and concentric with said tubular part is provided in the face of the collar directed there towards. Thus, the cells of said living tissues may populate the groove and be fixed therein.

Such a groove may have a depth and a width of the order of a millimeter.

In order to hold said implantable piece firmly in position before and during development of the cells in said piece, it is advantageous for this latter to comprise a removable cap, disposed on the outside of the skin and having points directed thereto, as well as clamping means for pressing the points of said cap against the skin. After complete cicatrisation, such a cap may be removed and replaced by a plug or similar.

The Figures of the accompanying drawing show how the invention may be implemented. In these Figures, identical references designate similar elements.

Figure 1:
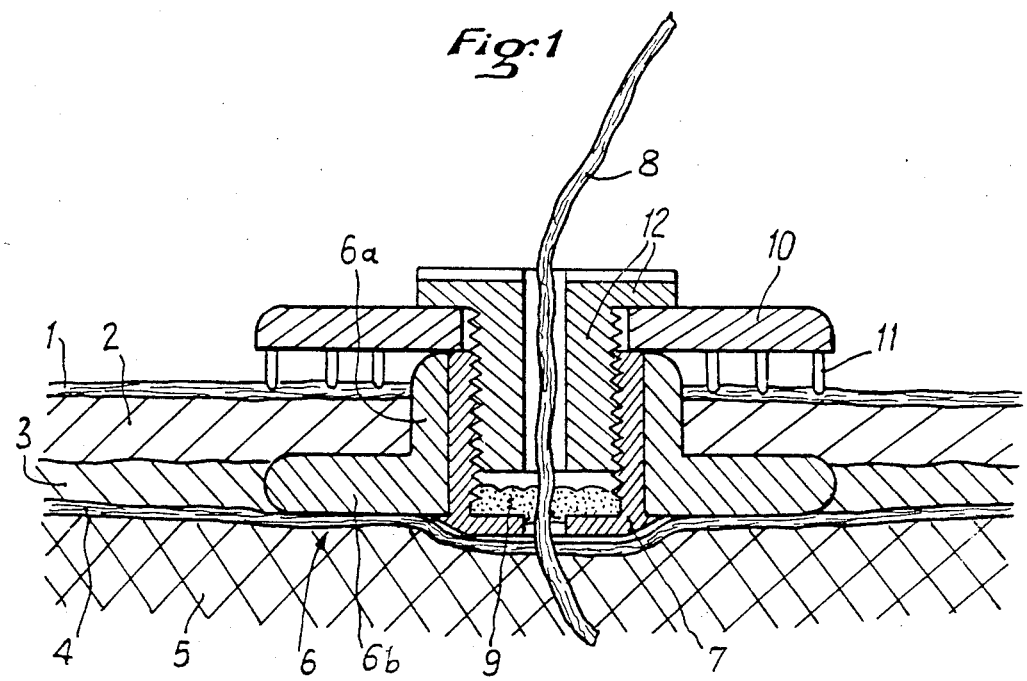
FIG. 1 shows, in a schematical axial section, a percutaneous passage device in accordance with the invention.
Figure 2:
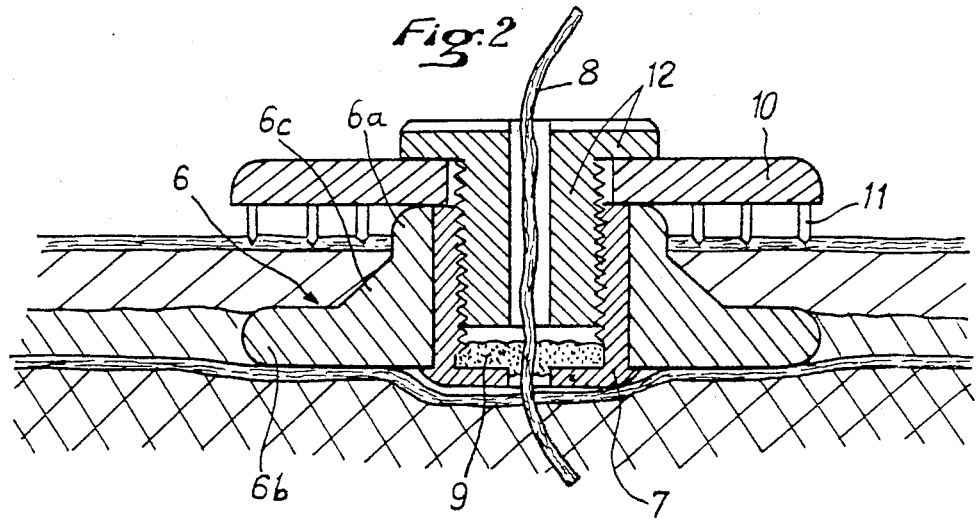
FIG. 2 shows, in a view similar to FIG. 1, a variant of the percutaneous passage device of the invention.

As shown in FIGS. 1 and 2, the skin, through which the embodiment described of the device of the invention is to allow a passage, comprises several superimposed layers which, from the outside towards the inside are the epiderm 1, the derm 2, a first layer of adipous tissue 3, the surface fascia 4 and a second layer of adipous tissue 5.

The percutaneous passage device of the invention comprises an implantable piece 6, formed of a tubular part 6a integral with a collar 6b at one of its ends. The thickness of the collar 6b may be of the order of 2 mm.

The implantable piece 6 is positioned by surgery so that its collar 6b is situated just below the derm 2, inside the first layer of adipous tissue 3 and above the surface fascia 4, and so that the tubular part 6a passes through the epiderm 1 and the derm 2.

Inside the tubular part 6a of the implantable piece 6 is disposed a liner 7, made from titanium or stainless steel for example, said liner 7 being firmly fixed to the piece 6, for example by bonding. The bottom of liner 7 is pierced so as to allow an element 8 to pass therethrough, such as a cable, pipe, etc . . . connecting the inside of a patient to the outside.

A sealing mass 9, made for example from a quick setting epoxy resin, provides the sealing between element 8 and liner 7.

So that the skin is held correctly in position after implantation and during the whole of the cicatrisation time, a washer 10 is provided having pointed pins 11 on its face intended to be directed towards the epiderm 1. These pins 11, for example, are spaced apart every 2 or 3 mm and have a diameter of 0.2 mm. Washer 10 is held in position by a screw 12 cooperating with an inner thread of the liner 7.

Pins 11 penetrate into the epiderm 1 which allows the skin to be efficiently held in position and applied against collar 16. In addition, the space formed between washer 11 and epiderm 1 promotes ventilation of the wound and so the cicatrisation.

After final cicatrisation, washer 10 and screw 12 are replaced by a protective plug (not shown), screwed into liner 7 and bearing against the free end of the tubular part 6a of the piece 6. Such a plug is readily removable for allowing the necessary checks.

In FIG. 1, the outer wall of the tubular part 6a is cylindrical. On the other hand, in the variants shown in FIGS. 2 and 3, the outer wall 6c of the tubular part 6a is conical, the base of this conical part being joined to the collar 6b. Such an embodiment is preferable for avoiding possible pockets in which the epithelial cells might form a sheath rejecting the implantable piece 6. The angle A of the cone may be between 30° and 60°.

Figure 3:
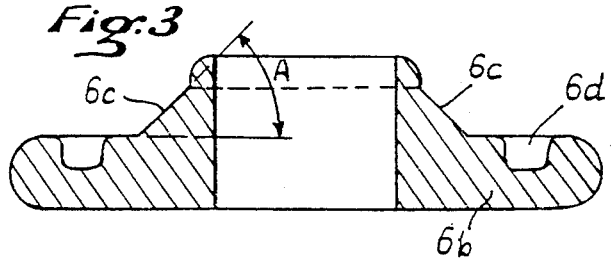
FIG. 3 illustrates, in axial section, another variant of the composite carbon piece of the percutaneous passage device of the invention.

Furthermore, as shown in FIG. 3, an annular cavity 6d may be provided in the face of collar 6b directed towards a tubular part 6a. Such an annular cavity 6d, preferably with rounded edges, may have a depth and a width of the order of 1 mm. It increases the tear strength, as soon as it is populated by the cells of the derm. Its inner edge may be situated at about 1 mm from the base of the cone 6c.

In accordance with the invention, so as to obtain the implantable piece 6 of FIGS. 1 to 3, a bed of carbon fiber sections of about 8 microns in diameter and a few millimeters in length is formed, for example by pouring these carbon fiber sections on a horizontal support. In this bed, the carbon fiber sections occupy more or less horizontal positions with random direction and freely rest on each other. Then, said bed is subjected to compression and vertical tufting, so that a felt of carbon fiber sections is obtained. This felt is then possibly subjected to an additional vertical compression for adjusting its specific mass to 0.25 g/cm$^3$.

The compressed felt is introduced into an enclosure containing town gas at a pressure of 15 torrs and cracking of said gas is carried out at 1000° C. Cracking of the gas is stopped when the specific mass of the felt reaches 1 g/cm$^3$.

Then a very porous material is obtained, with open pores. These pores have outside cross dimensions of about 0.2 mm to 0.005 mm.

In this material thus obtained, piece 6 is machined so that the tubular part 6a is parallel to the vertically tufted fibers and so that collar 6b is parallel to the initial horizontal fibers.

The machined base 6 is subjected to dust removal, to the action of an ultrasonic generator and to oxidization at a high temperature and for a few seconds.

After possible grafting of atoms and molecules promoting the fixing speed and/or adhesion of the cells of the derm (as mentioned above) and impregnation with nutritive serum, piece 6 is positioned in the above described way.

During cicatrisation, the implantable piece 6 will be integrated with the skin, mainly through the penetration of the fibroblasts of the derm into the whole thickness of collar 6b.

We claim:

1. Process for making a homogeneous monolithic material having pores communicating with each other, for use in fabricating a piece implantable by surgery in the adipose tissue of the skin, comprising the following steps:
   (a) forming a bed of carbon fiber sections whose length is at most equal to 30 mm, said carbon fiber sections freely resting on each other with random orientations;
   (b) compressing said bed so that its specific mass is between 0.05 and 0.3 g/cm$^3$, said compressed bed having said pores;
   (c) introducing said compressed bed into an enclosure containing hydrocarbonated gas, said hydrocarbonated gas penetrating into the pores of said compressed bed;
   (d) cracking said hydrocarbonated gas so that pyrocarbon is deposited on said fiber sections in said pores; and
   (e) continuing said cracking until the specific mass of said compressed bed is between 0.5 and 1.6 g/cm$^3$, thereby providing a uniform porous bed of pyrocarbon-coated fibers, wherein said pores communicate with each other.

2. The process of claim 1 wherein said bed of carbon fiber sections is subjected to tufting in a direction orthogonal to said bed.

3. The process of claim 1 wherein said material is machined and then subjected to the action of ultrasounds.

4. The process of claim 1 wherein said material is machined and then oxidized at high temperature in an oxygen atmosphere.

5. The process of claim 2 wherein the carbon fibers in said tufted bed have diameters in the range of 8 to 12 microns, wherein said tufted bed of carbon fibers is subjected to vertical compression, wherein said homogeneous monolithic material has pores having outside cross dimensions of about 0.2 to 0.005 mm, and wherein said homogeneous monolithic material is machined, subjected to the action of ultrasounds and then oxidized at high temperature in an oxygen atmosphere.

* * * * *